United States Patent [19]  [11]  3,971,822
Chibata et al.  [45] July 27, 1976

[54] ASPARTYL AMIDE SWEETENING AGENTS

[75] Inventors: Ichiro Chibata, Suita; Munetugu Miyoshi, Nishinomiya; Hiroshi Ito, Itami; Toshiyuki Fujii, Toyonaka; Keisuke Kawashima, Takatuki, all of Japan

[73] Assignee: Tanabe Seiyaku Co., Ltd., Osaka, Japan

[22] Filed: June 25, 1975

[21] Appl. No.: 590,020

[30] Foreign Application Priority Data
July 19, 1974 Japan............................... 49-83406
Sept. 17, 1974 Japan............................. 49-107293

[52] U.S. Cl. .................. 260/468 R; 260/112.5 R; 260/468 H; 260/486 R; 260/534 R; 260/534 M; 426/548
[51] Int. Cl.² ................ C07C 69/00; C07C 69/52; C07C 99/00
[58] Field of Search ....... 260/482 R, 484 R, 534 R, 260/534 M, 535 R, 561 R, 561 A, 112.5 R, 468 R, 468 H, 486 R; 426/548

[56] References Cited
UNITED STATES PATENTS
3,496,219 2/1970 Young............................. 260/482 R
3,907,766 9/1975 Fujino et al................. 260/112.5 R

*Primary Examiner*—Lewis Gotts
*Assistant Examiner*—Reginald J. Suyat
*Attorney, Agent, or Firm*—Jordan B. Bierman; Linda Bierman; Kenneth J. Stempler

[57] ABSTRACT

An ester compound of the formula:

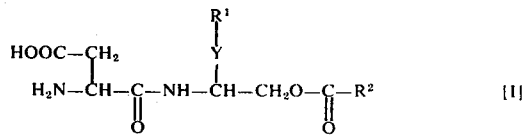

wherein $R^1$ is hydrogen or hydroxy, $R^2$ is alkyl of one to five carbon atoms, alkenyl of two to three carbon atoms, cycloalkyl of three to five carbon atoms or methylcycloalkyl of four to six carbon atoms and Y is alkylene of one to four carbon atoms, is disclosed. Several methods for preparing the compound[I] are also disclosed. The compound[I] is useful as a non-nutritive sweetening agent.

28 Claims, No Drawings

ASPARTYL AMIDE SWEETENING AGENTS

This invention relates to novel ester compounds and the use of said compounds as sweetening agents. More particularly, it relates to the compounds represented by the formula:

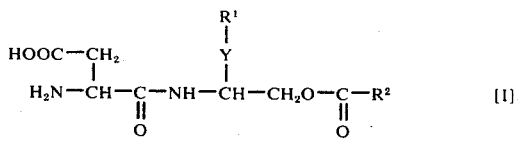

wherein R¹ is hydrogen or hydroxy, R² is alkyl of one to five carbon atoms, alkenyl of two to three carbon atoms, cycloalkyl of three to five carbon atoms or methylcycloalkyl of four to six carbon atoms, and Y is alkylene of one to four carbon atoms.

Although many substances have been proposed and/or tried to be used as artificial sweetening agents, most of them have not been used practically for their disadvantageous properties such as bitter aftertaste, toxic side effect, etc. Recently, it has been reported in Journal of the American Chemical Society, Vol. 91, pages 2684 – 2691 (1969) that lower alkyl ester, especially methyl ester of L-aspartyl-L-phenylalanine has a good sweetening property (100 to 200 times sweeter than sucrose). However, said ester also has a serious disadvantage that it is quite unstable in water and readily produces a diketopiperazine compound causing unpleasant taste.

The ester compounds[I] of the present invention are novel ester derivatives of N-aspartyl-aminoalkanol and show good and potent sweetening effect. Typical examples of said compounds are the ester of L-aspartyl-D-alaninol and propionic acid, the ester of L-aspartyl-D-alaninol and isobutyric acid, the ester of L-aspartyl-D-alaninol and pivalic acid, the ester of L-aspartyl-D-alaninol and 2-methylbutyric acid, the ester of L-aspartyl-D-alaninol and acrylic acid, the ester of L-aspartyl-D-alaninol and methacrylic acid, the ester of L-aspartyl-D-alaninol and cyclopropane carboxylic acid, the ester of L-aspartyl-D-alaninol and cyclobutane carboxylic acid, the ester of L-aspartyl-D-alaninol and 2-methylcyclobutane carboxylic acid, the ester of L-aspartyl-D-serinol and propionic acid and the ester of L-aspartyl-D-serinol and cyclopropane carboxylic acid. These compounds are 120, 145, 240, 150, 100, 130, 200, 220, 160, 160, 120 times sweeter than sucrose, respectively. Moreover, these compounds are stable against heat in water, and do not leave unpleasant aftertaste. Among the novel ester compounds[I] of the present invention, those having L-D or L-DL stereochemical configuration have specifically potent sweetening properties.

The compound[I] of the present invention can be prepared by condensing aspartic acid with a compound represented by the formula:

wherein R¹ and Y have the same meaning as defined above, followed by allowing the resultant compound to esterification with a compound represented by the formula:

$$R^2COOH \quad \text{[III]}$$

wherein R² has the same meaning as defined above.

α-Amino and β-carboxy groups of aspartic acid are protected throughout the condensation and esterification reactions with protecting groups such as tert-butyloxycarbonyl, tert-amyloxycarbonyl, o-nitrophenylsulphenyl, benzyloxycarbonyl or p-methoxybenzyloxycarbonyl group for α-amino group and tertbutyl or benzyl group for β-carboxy group. When R¹ is hydroxy group, it is protected throughout the condensation and esterification reactions with a protecting group such as tert-butyl or benzyl group.

The condensation reaction can be carried out in a conventional manner used for preparing peptide compounds, for example, by reacting aspartic acid α-p-nitrophenyl ester, aspartic acid α-N-hydroxysuccinimide ester, aspartic acid α-cyanomethyl ester or aspartic acid α-pentachlorophenyl ester with the compound[II] at −10° to 50°C, especially at 0° to 20°C, in a solvent. It is preferred to carry out the reaction in the presence of a catalyst such as N-hydroxybenzotriazole. Suitable examples of the solvent include tetrahydrofuran, ethyl acetate, chloroform, dioxane and dimethylformamide. The condensation reaction can be also carried out by reacting aspartic acid azide with the compound[II] at −30° to 10°C, especially at −15° to 0°C, in a solvent. Suitable examples of the solvent include dimethylformamide, chloroform and tetrahydrofuran.

The following esterification reaction can be carried out in a conventional manner used for esterification, for example, by reacting the compound obtained in the condensation reaction with an acid halide (e.g., acid chloride, acid bromide) or an acid anhydride corresponding to the compound[III] in the presence of a tertiary amine such as pyridine or triethylamine. It is preferred to carry out the reaction at −10° to 50°C, especially at 0° to 20°C, in a solvent. Suitable examples of the solvent include chloroform, dimethyformamide, pyridine and tetrahydrofuran. The esterification can be also carried out by reacting the compound obtained in the condensation reaction with the compound[III] in the presence of a condensing agent such as N,N′-dicyclohexylcarbodiimide and N,N′-carbonyldiimidazole. It is preferred to carry out the reaction at −20° to 50°C, especially at −5° to 20°C, in a solvent. Suitable examples of the solvent include chloroform, dimethylformamide and tetrahydrofuran.

The compound[I] can be obtained by elimination of protecting groups from the compound obtained in the esterification reaction. The elimination of the protecting groups can be carried out in a single step or if necessary in several steps according to the method well known in peptide chemistry. For example, when p-methoxybenzyloxycarbonyl, benzyloxycarbonyl and benzyl groups were employed as protecting groups, they can be eliminated by catalytic hydrogenation in methanol in the presence of a catalyst such as palladium-charcoal and palladium black. Furthermore, when tert-butyloxycarbonyl, tert-amyloxycarbonyl, o-nitrophenylsulphenyl, p-methoxybenzyloxycarbonyl and tert-butyl groups were employed, they can be eliminated by acidolysis, for example, with tri-fluoroacetic acid, a mixture of hydrogen chloride and dioxane, or a mixture of hydrogen chloride and acetic acid.

Alternatively, the compound[I] can be prepared by allowing the compound [II] to esterification with the compound [III], followed by condensing the resultant compound with aspartic acid.

α-Amino group of the compound [II] is protected throughout the esterification reaction with a protecting group such as tert-butyloxycarbonyl, tert-amyloxycarbonyl, o-nitrophenylsuphenyl, benzyloxycarbonyl or p-methoxybenzyloxycarbonyl group. When $R^1$ is hydroxy group, it is protected throughout the esterification and condensation reactions with a protecting group such as tert-butyl or benzyl group. Furthermore, α-amino and β-carboxy groups of aspartic acid are protected throughout the condensation reaction with protecting groups such as tert-butyloxycarbonyl, tert-amyloxycarbonyl, o-nitrophenylsulphenyl, benzyloxycarbonyl or p-methoxybenzyloxycarbonyl group for α-amino group and tert-butyl or benzyl group for β-carboxy group.

The above-mentioned esterification and condensation reactions can be carried out in accordance with the same manner as described in the first method.

The compounds[I] thus obtained are used as non-nutritive sweetening agents for foods, beverages, medical substances, or any other orally acceptable substance by adding one or more than two of the compounds [I] to the substance. Examples of such substances are as follows: carbonated or non-carbonated beverages; backed foods such as bread, crackers, pretzels, pastries and cake; milk derived products such as ice cream, ice milk, sherbets and custards; confectionary products such as chocolate candies and peanut candies, chewing gum tooth-paste, mouthwash; medical substances such as a tablet, capsule, powder, elixier and a syrup.

The amount of the compound[I] to be employed is not critical so long as an effective amount is used. Generally, an effective amount is that amount which provides a sense of sweetness comparable to that afforded by sucrose at a given usage rate. The amount of the compound[I] to be used will also depend upon such variables as person's preference, the purpose of sweetening and other factors. The compound [I] serving as the present active agent can be employed as sole agent. Alternatively, the compound[I] can be employed jointly with other known sweetening agents.

Practical and presently preferred embodiments of the present invention will be illustrated in the following examples.

EXPERIMENT 1

Each of the compounds shown in the following Table 1 was dissolved in water until the sweetness of the solution reached a comparable level to an aqueous solution containing 4 % of sucrose. Sweetness of the solutions were judged by a taste panel consisting of 10 persons. Potency of sweetness of the compounds tested was compared by relative ratio of the concentration to 4 % aqueous sucrose solution. The results are shown in Table 1 in terms of sweetness ratio which was calculated by:

$$\text{Sweetness ratio} = \frac{\text{Concentration of sucrose solution}}{\text{Concentration of test compound at which the sweetness is comparable to sucrose solution}}$$

Table 1

$$\begin{array}{c} \text{HOOC}-\text{CH}_2 \quad\quad\quad R^1 \\ | \quad\quad\quad\quad\quad | \\ \text{H}_2\text{N}-\text{CH}-\overset{\text{O}}{\underset{\|}{\text{C}}}-\text{NH}-\text{CH}-\text{CH}_2\text{O}-\overset{\text{O}}{\underset{\|}{\text{C}}}-R^2 \end{array}$$

| Test compound No. | —Y—$R^1$ | $R^2$ | Stereochemical configuration | Sweetness ratio |
|---|---|---|---|---|
| 1 | —$CH_3$ | —$CH_3$ | L-D | 75 |
| 2 | —$CH_3$ | —$CH_2CH_3$ | L-D | 120 |
| 3 | —$CH_3$ | —$CH_2CH_2CH_3$ | L-D | 60 |
| 4 | —$CH_3$ | —$CH(CH_3)_2$ | L-D | 145 |
| 5 | —$CH_3$ | —$C(CH_3)_3$ | L-D | 240 |
| 6 | —$CH_3$ | —$CH_2CH(CH_3)_2$ | L-D | 50 |
| 7 | —$CH_3$ | —CHCH$_2$CH$_3$ with CH$_3$ branch | L-D | 150 |
| 8 | —$CH_3$ | —CHCH$_2$CH$_2$CH$_3$ with CH$_3$ branch | L-D | 50 |
| 9 | —$CH_3$ | —CH=$CH_2$ | L-D | 100 |
| 10 | —$CH_3$ | —C=$CH_2$ with CH$_3$ branch | L-D | 130 |
| 11 | —$CH_3$ | cyclopropyl | L-D | 200 |
| 12 | —$CH_3$ | cyclobutyl | L-D | 220 |

Table 1-continued

| | | | | |
|---|---|---|---|---|
| 13 | —CH$_3$ | ◁ | L-D | 60 |
| 14 | —CH$_3$ | ⊲-CH$_3$ (with CH$_3$) | L-D | 60 |
| | | | L-D | 160 |
| 15 | —CH$_3$ | ◇ | | |
| 16 | —CH(CH$_3$)$_2$ | —CH$_3$ | L-D | 60 – 75 |
| 17 | —CH(CH$_3$)$_2$ | —CH$_2$CH$_3$ | L-D | 60 – 75 |
| 18 | —CH$_2$OH | —CH$_2$CH$_3$ | L-D | 160 |
| 19 | —CH$_2$OH | ◁ | L-D | 120 |
| 20 | —CH$_2$OH | ◇ | L-D | 65 |

EXPERIMENT 2

Aqueous solutions, each of them contains 0.05 % of one of the compounds shown in Table 1 and an aqueous solution containing 0.05 % of L-aspartyl-L-phenylalanine methyl ester were prepared. The solutions were heated at 95°C for 1 hour. Each of the solutions was compared with the corresponding un-heated solution by a taste panel consisting of 10 persons. All of the ten persons found that the solutions of the compounds of the present invention were substantially unchanged in taste by heating, whereas, in the case of L-aspartyl-L-phenylalanine methyl ester, unpleasant taste was produced by heating.

EXPERIMENT 3

Aqueous solutions, each of them contains one % of one of the compounds shown in Table 1 were prepared and heated at 90°C for 2 hours. The solution was then subjected to paper chromatography (solvent for development; butanol : acetic acid : water = 4 : 1 : 1), thin layer chromatography (solvent for development; butanol : acetic acid : water = 4 : 1 : 1) and filter paper electrophoresis (pH 3.8, 2000 V/2 hours). In any of these analyses, no spot other than that of the test compounds was detected, which shows all of the compounds tested are stable against heat in water.

EXAMPLE 1

The ester of L-aspartyl-D-alaninol and acetic acid (the compound [I]: R$^1$ = H, R$^2$ = —CH$_3$, Y = —CH$_2$—)

1. 4.8 g of N-benzyloxycarbonyl-β-benzyl-L-aspartic acid α-p-nitrophenyl ester were added to 30 ml of dimethylformamide containing 0.75 g of D-alaninol and 1.5 g of N-hydroxybenzotriazole at a temperature lower than 15°C. The mixture was stirred at 20°C for 30 minutes. The reaction solution was poured into ice-water and the mixture was extracted with ethyl acetate. The extract was washed with 2 % hydrochloric acid, 5 % sodium carbonate, 3 % aqueous ammonia and an aqueous sodium chloride solution, successively. Then, the solvent was evaporated from the extract under reduced pressure. The crystalline residue thus obtained was recrystallized from a mixture of ethyl acetate and petroleum ether, whereby 3.0 g of N-benzyloxycarbonyl-β-benzyl-L-aspartyl-D-alaninol were obtained. Yield: 72.5 % M.p. 110° – 111°C 2. 3.0 g of N-benzyloxycarbonyl-β-benzyl-L-aspartyl-D-alaninol were dissolved in 20 ml of dried pyridine. 1.75 g of acetyl chloride were added dropwise to the solution at a temperature lower than 15°C. The mixture was stirred at 15° – 20°C for 2 hours. Pyridine was removed by evaporation from the reaction solution under reduced pressure and the residue was extracted with ethyl acetate. The extract was washed with 2 % hydrochloric acid, 5 % sodium carbonate and an aqueous sodium chloride solution, successively. Then, the extract was dried and concentrated under reduced pressure. The crystalline residue thus obtained was recrystallized from a mixture of ethyl acetate and petroleum ether, whereby 2.2 g of the ester of N-benzyloxycarbonyl-β-benzyl-L-aspartyl-D-alaninol and acetic acid were obtained. Yield: 66.5 % M.p. 101° – 103°C 3. 1.8 g of the ester of N-benzyloxycarbonyl-β-benzyl-L-aspartyl-D-alaninol and acetic acid were dissolved in 50 ml of methanol and 0.1 g of 5 % palladium-charcoal was added to the solution. Hydrogen gas was introduced into the mixture until the absorption of hydrogen was completed. Then, the catalysts were removed by filtration and the filtrate was evaporated to remove solvent under reduced pressure. The residue thus obtained was recrystallized from a mixture of methanol and ether. 0.76 g of the ester of L-aspartyl-D-alaninol and acetic acid was obtained. Yield: 82 % M.p. 146° – 159°C

EXAMPLE 2

The ester of L-aspartyl-D-alaninol and propionic acid (the compound [I]: R$^1$ = H, R$^2$ = —CH$_2$CH$_3$, Y = —CH$_2$—)

1. 3.0 g of N-benzyloxycarbonyl-D-alaninol were dissolved in 50 ml of dried pyridine and 2.8 g of propionyl chloride were added to the solution. The mixture was stirred at 15° – 20°C for 2 hours. Pyridine was removed by evaporation from the reaction solution under reduced pressure and the residue was extracted with ethyl acetate. The extract was washed with 2 % hydrochloric acid, 5 % sodium carbonate and an aqueous sodium chloride solution, successively. Then, the extract was dried and concentrated under reduced pressure. The residue thus obtained was recrystallized from a mixture of ethyl acetate and petroleum ether, whereby 1.2 g of the ester of N-benzyloxycarbonyl-D-alaninol and propionic acid were obtained. Yield: 90 % M.p. 52° – 54°C 2. One g of the ester of N-benzyloxycarbonyl-D-alaninol and propionic acid was dissolved in 50 ml of methanol and 0.1 g of 5 % palladium-charcoal was added to the solution. Hydrogen gas was introduced into the mixture until the absorption of hydrogen was completed. Then, the catalysts were removed by filtration and the filtrate was evaporated to remove solvent under reduced pressure, whereby 0.7 g of the ester of D-alaninol and propionic acid was obtained as an oil. Yield: 100 %

3. 0.7 g of the ester of D-alaninol and propionic acid and 2 g of N-benzyloxycarbonyl-$\beta$-benzyl-L-aspartic acid $\alpha$-p-nitrophenyl ester were dissolved in 20 ml of dimethylformamide and 0.6 g of N-hydroxybenzotriazole was added to the solution. The mixture was stirred at 15°C for 30 minutes. The reaction solution was extracted with ethyl acetate and the extract was washed with M-hydrochloric acid, 5 % sodium bicarbonate and a saturated aqueous sodium chloride solution, successively. Then, the extract was dried and concentrated under reduced pressure. The residue thus obtained was recrystallized from a mixture of ether and petroleum ether, whereby 0.66 g of the ester of N-benzyloxycarbonyl-$\beta$-benzyl-L-aspartyl-D-alaninol and propionic acid was obtained. Yield: 70.2 % M.p. 85° – 88°C 4. 4.0 g of the ester of N-benzyloxycarbonyl-$\beta$-benzyl-L-aspartyl-D-alaninol and propionic acid were dissolved in 100 ml of methanol and 0.2 g of 5 % palladium-charcoal was added to the solution. Hydrogen gas was introduced into the mixture until the absorption of hydrogen was completed. Then, the catalysts were removed by filtration and the filtrate was evaporated to remove solvent under reduced pressure. The crystalline residue thus obtained was recrystallized from a mixture of methanol and ether. 2.2 g of the ester of L-aspartyl-D-alaninol and propionic acid were obtained. Yield: 90 % M.p. 155° – 156°C (decomp.)

EXAMPLE 3

The ester of L-aspartyl-D-alaninol and isobutyric acid (the compound [I]: $R^1 = H$, $R^2 = -CH(CH_3)_2$, $Y = -CH_2-$)

1. 4.14 g of N-benzyloxycarbonyl-$\beta$-benzyl-L-aspartyl-D-alaninol were dissolved in 20 ml of dried pyridine and 3.2 g of isobutyryl chloride were added dropwise to the solution at a temperature lower than 15°C. The mixture was stirred at 15° – 20°C for 2 hours. Then, the reaction solution was treated in the same manner as described in Example 1-(2), whereby 4.1 g of the ester of N-benzyloxycarbonyl-$\beta$-benzyl-L-aspartyl-D-alaninol and isobutyric acid were obtained. Yield: 84.8 % M.p. 92° – 94°C 2. 4.0 g of the ester of N-benzyloxycarbonyl-$\beta$-benzyl-L-aspartyl-D-alaninol and isobutyric acid were dissolved in 100 ml of methanol and 0.2 g of 5 % palladium-charcoal was added to the solution. Hydrogen gas was intoduced into the mixture until the absorption of hydrogen was completed. Then, the reaction solution was treated in the same manner as described in Example 1-(3). 2.0 g of the ester of L-aspartyl-D-alaninol and isobutyric acid were obtained. Yield: 93 % M.p. 154° – 155°C

EXAMPLE 4 – 24

The following compounds were obtained in accordance with the same manner as described in Example 1 or 2.

4. The ester of L-aspartyl-D-alaninol and butyric acid (the compound [I]: $R^1 = H$, $R^2 = -CH_2CH_2CH_3$, $Y = -CH_2-$)
M.p. 151° – 152°C 5. The ester of L-aspartyl-D-alaninol and pivalic acid (the compound [I]: $R^1 = H$, $R^2 = -C(CH_3)_3$, $Y = -CH_2-$)
M.p. 145° – 147°C (decomp.)

6. The ester of L-aspartyl-D-alaninol and valeric acid (the compound [I]: $R^1 = H$, $R^2 = -CH_2CH_2CH_2CH_3$, $Y = -CH_2-$)
M.p. 157° – 159°C (decomp.)

7. The ester of L-aspartyl-D-alaninol and isovaleric acid (the compound [I]: $R^1 = H$, $R^2 = -CH_2CH(CH_3)_2$, $Y = -CH_2-$)
M.p. 163° – 166.5°C (decomp.)

8. The ester of L-aspartyl-D-alaninol and 2-methylbutyric acid (the compound [I]: $R^1 = H$,

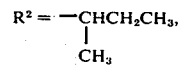

$Y = -CH_2-$)
M.p. 115° – 119°C (decomp.)

9. The ester of L-aspartyl-D-alaninol and 2-ethylbutyric acid (the compound [I]: $R^1 = H$, $R^2 = -CH(CH_2CH_3)_2$, $Y = -CH_2-$)
M.p. 126.5° – 127.5°C (decomp.)

10. The ester of L-aspartyl-D-alaninol and cyclopropane carboxylic acid (the compound [I]: $R^1 = H$,

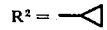

$Y = -CH_2-$)
M.p. 146.5° – 149°C (decomp.)

11. The ester of L-aspartyl-D-alaninol and cyclobutane carboxylic acid (the compound [I]: $R^1 = H$,

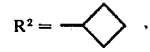

$Y = -CH_2-$)
M.p. 168.5° – 170°C (decomp.)

12. The ester of L-aspartyl-D-alaninol and cyclopentane carboxylic acid (the compound [I]: $R^1 = H$,

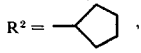

Y = —CH$_2$—)
M.p. 162° – 165°C (decomp.)

13. The ester of L-aspartyl-D-alaninol and 2-methyl-cyclopropane carboxylic acid (the compound [I]: R$^1$ = H,

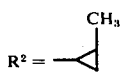

Y = —CH$_2$—)
M.p. 151° – 153°C (decomp.)

14. The ester of L-aspartyl-D-alaninol and 2-methyl-cyclobutane carboxylic acid (the compound [I]: R$^1$ = H,

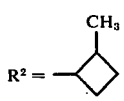

Y = —CH$_2$—)
M.p. 134° – 135°C (decomp.)

15. The ester of L-aspartyl-DL-α-aminobutanol and acetic acid (the compound [I]: R$^1$=H, R$^2$ = —CH$_3$, Y = —CH$_2$CH$_2$—)
M.p. 112° – 117°C 16. The ester of L-aspartyl-DL-α-aminobutanol and propionic acid (the compound [I]: R$^1$ = H, R$^2$ = —CH$_2$CH$_3$, Y = —CH$_2$CH$_2$—)
M.p. 128° – 130°C 17. The ester of L-aspartyl-DL-α-aminobutanol and isobutyric acid (the compound [I]: R$^1$ = H, R$^2$ = —CH(CH$_3$)$_2$, Y = —CH$_2$CH$_2$—)
M.p. 134° – 138°C 18. The ester of L-aspartyl-DL-α-aminobutanol and cyclopropane carboxylic acid (the compound [I]: R$^1$ = H,

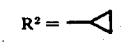

Y = —CH$_2$CH$_2$—)
M.p. 90° – 92°C (decomp.)

19. The ester of L-aspartyl-DL-α-aminobutanol and cyclobutane carboxylic acid (the compound [I]: R$^1$ = H,

Y = —CH$_2$CH$_2$—)
M.p. 94.5° – 101°C (decomp.)

20. The ester of L-aspartyl-D-valinol and acetic acid (the compound [I]: R$^1$ = H, R$^2$ = —CH$_3$,

Y = —CHCH$_2$—)
    |
    CH$_3$

M.p. 174° – 175°C

21. The ester of L-aspartyl-D-valinol and propionic acid (the compound [I]: R$^1$ = H, R$^2$ = —CH$_2$CH$_3$,

Y = —CHCH$_2$—)
    |
    CH$_3$

M.p. 138° – 141°C

22. The ester of L-aspartyl-D-valinol and isobutyric acid (the compound [I]: R$^1$ = H, R$^2$ = —CH(CH$_3$)$_2$,

Y = —CHCH$_2$—)
    |
    CH$_3$

M.p. 148° – 151°C

23. The ester of L-aspartyl-D-valinol and cyclopropane carboxylic acid (the compound [I]: R$^1$ = H,

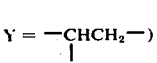

Y = —CHCH$_2$—)
    |
    CH$_3$

M.p. 129° – 133°C (decomp.)

24. The ester of L-aspartyl-D-valinol and cyclobutane carboxylic acid (the compound [I]: R$^1$ = H,

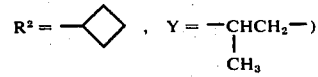

M.p. 94.5° – 97°C (decomp.)

EXAMPLE 25

The ester of L-aspartyl-D-serinol and propionic acid (the compound [I]: R$^1$ = —OH, R$^2$ = —CH$_2$CH$_3$, Y = —CH$_2$—)

1. 4.8 g of N-benzyloxycarbonyl-β-benzyl-L-aspartic acid α-p-nitrophenyl ester were added to 30 ml of dimethylformamide containing 2.2 g of O-benzyl-D-serinol hydrochloride, 1.4 ml of triethylamine and 1.4 g of N-hydroxybenzotirazole at a temperature lower than 10°C. The mixture was stirred at 15° – 20 C for 30 minutes. The reaction solution was poured into ice-water and the mixture was extracted with ethyl acetate. The extract was washed with 3 % aqueous ammonia, 0.5 M citric acid and an aqueous sodium chloride solution, successively. Then, the extract was dried and concentrated under reduced pressure. The crystalline residue thus obtained was recrystallized from a mixture of ethyl acetate and petroleum ether, whereby 3.5 g of N-benzyloxycarbonyl-β-benzyl-L-aspartyl-O-benzyl-D-serinol were obtained. Yield: 67.3 % M.p. 100° – 103°C 2. 1.6 g of N-benzyloxycarbonyl-β-benzyl-L-aspartyl-O-benzyl-D-serinol were dissolved in 20 ml of dried pyridine and 0.84 g of propionyl chloride was added dropwise to the solution at 15°–20°C. The mixture was stirred at 15°–20°C for 70 minutes. Pyridine was removed by evaporation from the reaction solution under reduced pressure. The residue thus obtained was extracted with ethyl acetate and the extract was washed with M-hydrochloric acid, a saturated aqueous sodium bicarbonate solution and a saturated aqueous sodium chloride solution, successively. Then, the extract was dried and concentrated under reduced pressure. The residue thus obtained was dissolveed in 3 ml of a mixture of ethyl acetate and benzene (2 : 8) and the solution was poured onto a column of silica gel. Then, the column was eluted with a mixture of ethyl acetate and benzene (2 : 8) and the eluate was concentrated under reduced pressure. The crystalline residue thus obtained was recrystallized from a mixture of ethyl acetate and petroleum ether, whereby 1.45 g of the ester of N-benzyloxycarbonyl-β-benxyl-L-aspartyl-O-benzyl-D-serinol and propionic acid were obtained. Yield: 82 % M.p. 108°–109°C 3. 1.4 g of the ester of N-benzyloxycarbonyl-β-benzyl-L-aspartyl-O-benzyl-D-serinol and propionic acid were dissolved in a mixture of 100 ml of methanol and 20 ml of water, and 0.3 g of 5 % palladium-charcoal was added to the solution. Hydrogen gas was introduced into the mixture until the absorption of hydrogen was completed. Then, the catalysts were removed by filtration and the filtrate was evaporated to remove solvent under reduced pressure. The crystalline residue thus obtained was recrystallized from hot methanol. 0.52 g of the ester of L-aspartyl-D-serinol and propionic acid was obtained. Yield: 81.3 % M.p. 190°–191°C

EXAMPLE 26 – 33

The following compounds were obtained in accordance with the same manner as described in Example 25. 26. The ester of L-aspartyl-D-serinol and acetic acid (the compound [I]: $R^1 = -OH$, $R^2 = -CH_3$, $Y = -CH_2-$)
M.p. 206.5°–207°C (decomp.)

27. The ester of L-aspartyl-D-serinol and butyric acid (the compound [I]: $R^1 = -OH$, $R^2 = -CH_2CH_2CH_3$, $Y = -CH_2-$)
M.p. 197°–199°C (decomp.)

28. The ester of L-aspartyl-D-serinol and isobutyric acid (the compound [I]: $R^1 = -OH$, $R^2 = -CH(CH_3)_2$, $Y = -CH_2-$)
M.p. 209°–211°C (decomp.)

29. The ester of L-aspartyl-D-serinol and 2-methylbutyric acid (the compound [I]: $R^1 = -OH$, $R^2 = -\underset{\underset{CH_3}{|}}{C}HCH_2CH_3$, $Y = -CH_2-$)

M.p. 195°–196°C (decomp.)

30. The ester of L-aspartyl-D-serinol and pivalic acid (the compound [I]: $R^1 = -OH$, $R^2 = -C(CH_3)_3$, $Y = -CH_2-$)
M.p. 203°–204°C (decomp.)

31. The ester of L-aspartyl-D-serinol and cyclopropane carboxylic acid (the compound [I]: $R^1 = -OH$,

$Y = -CH_2-$)
M.p. 172.5°–175°C (decomp.)

32. The ester of L-aspartyl-D-serinol and cyclobutane carboxylic acid (the compound [I]: $R^1 = -OH$,

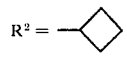

$Y = -CH_2-$)
M.p. 185°–190°C (decomp.)

33. The ester of L-aspartyl-D-serinol and cyclopentane caboxylic acid (the compound [I]: $R^1 = -OH$,

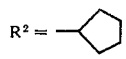

$Y = -CH_2-$)
M.p. 191.5°–192.5°C (decomp.)

EXAMPLE 34

The ester of L-aspartyl-D-alaninol and propionic acid (the compound [I]: $R^1 = H$, $R^2 = -CH_2CH_3$, $Y = -CH_2-$)

1. 4.15 g of N-tert-butyloxycarbonyl-β-benzyl-L-aspartic acid α-N-hydroxysuccinimide ester in 30 ml of tetrahydrofuran were added to 0.75 g of D-alaninol in 20 ml of tetrahydrofuran. The mixture was stirred at 15°–20°C for 2 hours. Tetrahydrofuran was removed by evaporation under reduced pressure. The residue thus obtained was dissolved in ethyl acetate and the solution was washed with M-hydrochloric acid, 5 % aqueous sodium bicarbonate and an aqueous sodium chloride solution successively. Then, the solution was dried and concentrated under reduced pressure, whereby 3.7 g of N-tert-butyloxycarbonyl-β-benzyl-L-aspartyl-D-alaninol were obtained as an oil.

2. 1.8 g of N-tert-butyloxycarbonyl-β-benzyl-L-aspartyl-D-alaninol were dissolved in 20 ml of dried pyridine and 1.3 g of propionic anhydride were added to the solution under ice-cooling. The mixture was stired at 15°–20°C for 3 hours. The reaction solution was poured into ice-water and the mixture was extracted with ethyl acetate. The extract was washed with M-hydrochloric acid and water, successively. Then, the extract was dried and concentrated under reduced pressure. The oil thus obtained was dissolved in 3 ml of a mixture of ethyl acetate and benzene (4 : 6) and the solution was poured onto a column of silica gel. Then, the column was eluted with a mixture of ethyl acetate and benzene (4 : 6). The eluate was concentrated under reduced pressure, whereby 1.9 g of the ester of N-tert-butyloxycarbonyl-β-benzyl-L-aspartyl-D-alaninol and propionic acid were obtained as an oil.

3. 1.5 g of the ester of N-tert-butyloxycarbonyl-β-benzyl-L-aspartyl-D-alaninol and propionic acid were dissolved in 20 ml of a solution of 2M-hydrogen chloride in acetic acid. The solution was stirred at 15°–20°C for 1 hour. The reaction solution was poured into ice-water. The mixture was neutralized with sodium bicarbonate and extracted with ethyl acetate. The extract was washed with water, dried, and then concentrated under reduced pressure. The residue thus obtained was dissolved in 30 ml of methanol and 0.1 g of 5 % palladium-charcoal was added to the solution. Hydrogen gas was intoduced into the mixture until the absorption of hydrogen was completed. Then, the catalysts were removed by filtration and the filtrate was concentrated under reduced pressure. The crystalline residue thus obtained was recrystallized from a mixture of methanol and ether. 0.9 g of the ester of L-aspartyl-D-alaninol and propionic acid was obtained. M.p. 155° – 156°C (decomp.)

EXAMPLE 35

The ester of L-aspartyl-D-alaninol and acetic acid (the compound [I]: $R^1 = H$, $R^2 = -CH_3$, $Y = -CH_2-$)

1. 8.4 g of N-benzyloxycarbonyl-β-tert-butyl-L-aspartic acid α-N-hydroxysuccinimide ester were dissolved in 100 ml of chloroform and 1.5 g of D-alaninol in 15 ml of dimethylformamide were added to the solution. The mixture was stirred at 15° – 20°C for 2 hours. The reaction solution was treated in the same manner as described in Example 34-(1), whereby 2.0 g of N-benzyloxycarbonyl-β-tert-butyl-L-aspartyl-D-alaninol were obtained as an oil.

2. 1.8 g of N-benzyloxycarbonyl-β-tert-butyl-L-aspartyl-D-alaninol were dissolved in 20 ml of dried pyridin and 1.2 g of acetic anhydride were added to the solution under ice-cooling. The mixture was stirred at 15° – 20°C for 3 hours. The reaction solution was treated in the same manner as described in Example 34-(2), whereby 2.0 g of the ester of N-benzyloxycarbonyl-β-tert-butyl-L-aspartyl-D-alaninol and acetic acid were obtained as an oil.

3. 1.5 g of the ester of N-benzyloxycarbonyl-β-tert-butyl-L-aspartyl-D-alaninol and acetic acid were dissolved in 20 ml of a solution of 2M-hydrogen chloride in acetic acid. The solution was stirred at 15° – 20°C for 1 hour. The reaction solution was poured into ice-water and the mixture was extracted with ethyl acetate. The extract was washed with water, dried and then concentrated under reduced pressure. The residue thus obtained was dissolved in 30 ml of methanol and 0.1 g of 5 % paladium-charcoal was added to the solution. Hydrogen gas was introduced into the mixture until the absorption of hydrogen was completed. The reaction solution was treated in the same manner as described in Example 34-(3). 0.72 g of the ester of L-aspartyl-D-alaninol and acetic acid was obtained. M.p. 146° – 149°C

EXAMPLE 36

The ester of L-aspartyl-D-alaninol and acrylic acid (the compound [I]: $R^1 = H$, $R^2 = -CH=CH_2$, $Y = -CH_2-$)

1. 6.3 g of N-tert-butyloxycabonyl-β-tert-butyl-L-aspartic acid α-N-hydroxysuccinimide ester were dissolved in 45 ml of ethyl acetate and 1.34 g of D-alaninol in 5 ml of ethyl acetate were added to the solution. The mixture was stirred at 15° – 20°C for 2 hours. The reaction solution was treated in the same manner as described in Example 34-(1), whereby 5.6 g of N-tert-butyloxycarbonyl-β-tert-butyl-L-aspartyl-D-alaninol were obtained as an oil.

2. 3.1 g of N-tert-butyloxycarbonyl-β-tert-butyl-L-aspartyl-D-alaninol were dissolved in 30 ml of dried pyridine and 1.7 g of acrylic anhydride were added to the solution under ice-cooling. The mixture was stirred at 15° – 20°C for 1 hour. Pyridine was removed by evaporation from the reaction solution under reduced pressure. The oil thus obtained was dissolved in ethyl acetate and the solution was washed with a saturated aqueous sodium bicarbonate solution, water, 0.5 M citric acid and water, successively. Then, the solution was dried and concentrated under reduced pressure. The oil thus obtained was dissolved in 5 ml of a mixture of benzene and ethyl (4 : 1) and the solution was poured onto a column of silica gel. Then, the column was eluted with a mixture of benzene and ethyl acetate (4 : 1). The eluate was concentrated under reduced pressure, whereby 3.4 g of the ester of N-tert-butyloxycarbonyl-β-tert-butyl-L-aspartyl-D-alaninol and acrylic acid were obtained as an oil. Yield: 97.8 %

3. A few drops of anisole were added to 1.6 g of the ester of N-tert-butyloxycarbonyl-β-tert-butyl-L-aspartyl-D-alaninol and acrylic acid. 20 ml of trifluoroacetic acid were added dropwise to the mixture under ice-cooling. The mixture was stirred at 15° – 20°C for 70 minutes. The reaction solution was concentrated under reduced pressure. 100 ml of anhydrous ether was added to the residue thus obtained. Crude crystals were obtained by filtration and dissolved in water. The solution was passed through a column of Amberlite IR-45 (OH - form) (manufactured by Rohm & Haas Co.) and the effluent was lyophylized. 0.55 g of the ester of L-aspartyl-D-alaninol and acrylic acid was obtained as white powder. Yield: 75.3 % M.p. 226°C (decomp.)

EXAMPLE 37

In accordance with the same manner as described in Example 36, the ester of L-aspartyl-D-alaninol and methacrylic acid (the compound [I]: $R^1 = H$,

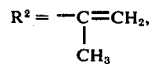

$Y = -CH_2-$) was obtained. M.p. 230°C (decomp.)

EXAMPLE 38

0.15 g of the ester of L-aspartyl-D-alaninol and acetic acid were dissolved in 100 ml of hot water in which 1.7 g of instant coffee was dissolved. The coffee thus obtained was almost equivalent in sweetness to the coffee which was prepared by adding 10 g of sucrose instead of said ester.

EXAMPLE 39

0.1 g of the ester of L-aspartyl-D-alaninol and propionic acid was dissolved in a small amount of water. The solution was sprinkled on the surface of a grapefruit cut into two pieces, whereby the grapefruit was well sweetened.

EXAMPLE 40

One liter of fruit juice of *Citrus Unshiu*, 300 ml of fruit juice of *Citrus Natshudaidai*, 3 g of citric acid, 5 ml of orange essence, 5 g of malic acid and 2.9 g of the ester of L-aspartyl-D-alaninol and isobutyric acid were mixed. The mixture was diluted with water to bring the total volume to 4 liters, whereby a sweet and delicious orange juice preparation was obtained.

What we claim is:

1. A compound of the formula:

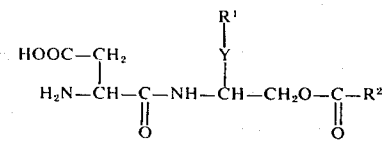

wherein R¹ is hydrogen or hydroxy, R² is alkyl of one to five carbon atoms, alkenyl of two to three carbon atoms, cycloalkyl of three to five carbon atoms or methylcycloalkyl of four to six carbon atoms, and Y is alkylene of one to four carbon atoms.

2. The compound as claimed in claim 1, wherein R¹ is hydrogen or hydroxy, R² is selected from the group consisting of methyl, ethyl, propyl, isopropyl, butyl, isobutyl, sec-butyl, tert-butyl, pentyl and 1-methylbutyl, and Y is selected from the group consisting of methylene, ethylene, 1-methylethylene, 1-methylpropylene and 2-methylpropylene.

3. The compound as claimed in claim 1, wherein R¹ is hydrogen or hydroxy, R² is vinyl or isopropenyl, and Y is selected from the group consisting of methylene, ethylene, 1-methylethylene, 1-methylpropylene and 2*methylpropylene.

4. The compound as claimed in claim 1, wherein R¹ is hydrogen or hydroxy, R² is selected from the group consisting of cyclopropyl, cyclobutyl, cyclopentyl, 2-methylcyclopropyl and 2-methylcyclobutyl, and Y is selected from the group consisting of methylene, ethylene, 1-methylethylene, 1-methylpropylene and 2-methylpropylene.

5. The compound as claimed in claim 1, wherein the stereochemical configuration of said compound is L-D or L-DL.

6. The compound as claimed in claim 2, wherein the stereochemical configuration of said compound is L-D or L-DL.

7. The compound as claimed in claim 3, wherein the stereochemical configuration of said compound is L-D or L-DL.

8. The compound as claimed in claim 4, wherein the stereochemical configuration of said compound is L-D or L-DL.

9. The compound as claimed in claim 2, wherein R¹ is hydrogen, R² is methyl, Y is methylene, and the stereochemical configuration of said compound is L-D or L-DL.

10. The compound as claimed in claim 2, wherein R¹ is hydrogen, R² is ethyl, Y is methylene, and the stereochemical configuration of said compound is L-D or L-DL.

11. The compound as claimed in claim 2, wherein R¹ is hydrogen, R² is propyl, Y is methylene, and the stereochemical configuration of said compound is L-D or L-DL.

12. The compound as claimed in claim 2, wherein R¹ is hydrogen, R² is isopropyl, Y is methylene, and the stereochemical configuration of said compound is L-D or L-DL.

13. The compound as claimed in claim 2, wherein R¹ is hydrogen, R² is tert-butyl, Y is methylene, and the stereochemical configuration of said compound is L-D or L-DL.

14. The compound as claimed in claim 2, wherein R¹ is hydrogen, R² is isobutyl, Y is methylene, and the stereochemical configuratioin of said compound is L-D or L-DL.

15. The compound as claimed in claim 2, wherein R¹ is hydrogen, R² is sec-butyl, Y is methylene, and the stereochemical configuration of said compound is L-D or L-DL.

16. The compound as claimed in claim 2, wherein R¹ is hydrogen, R² is 1-methylbutyl, Y is methylene, and the stereochemical configuration of said compound is L-D or L-DL.

17. The compound as claimed in claim 2, wherein R¹ is hydrogen, R² is methyl, Y is 1-methylethylene, and the stereochemical configuration of said compound is L-D or L-DL.

18. The compound as claimed in claim 2, wherein R¹ is hydrogen, R² is ethyl, Y is 1-methylethylene, and the stereochemical configuration of said compound is L-D or L-DL.

19. The compound as claimed in claim 2, wherein R¹ is hydroxy, R² is ethyl, Y is methylene, and the stereochemical configuration is L-D or L-DL.

20. The compound as claimed in claim 3, wherein R¹ is hydrogen, R² is vinyl, Y is methylene, and the stereochemical configuration of said compound is L-D or L-DL.

21. The compound as claimed in claim 3, wherein R¹ is hydrogen, R² is isopropenyl, Y is methylene, and the stereochemical configuration of said compound is L-D or L-DL.

22. The compound as claimed in claim 4, wherein R¹ is hydrogen, R² is cyclopropyl, Y is methylene, and the stereochemical configuration of said compound is L-D or L-DL.

23. The compound as claimed in claim 4, wherein R¹ is hydrogen, R² is cyclobutyl, Y is methylene, and the stereochemical configuration of said compound is L-D or L-DL.

24. The compound as claimed in claim 4, wherein R¹ is hydrogen, R² is cyclopentyl, Y is methylene, and the stereochemical configuration of said compound is L-D or L-DL.

25. The compound as claimed in claim 4, wherein R¹ is hydrogen, R² is 2-methylcyclopropyl, Y is methylene, and the stereochemical configuration of said compound is L-D or L-DL.

26. The compound as claimed in claim 4, wherein R¹ is hydrogen, R² is 2-methylcyclobutyl, Y is methylene, and the stereochemical configuration of said compound is L-D or L-DL.

27. The compound as claimed in claim 4, wherein R¹ is hydroxy, R² is cyclopropyl, Y is methylene, and the stereochemical configuration of said compound is L-D or L-DL.

28. The compound as claimed in claim 4, wherein R¹ is hydrogen, R² is cyclobutyl, Y is methylene, and the stereochemical configuration of said compound is L-D or L-DL.

* * * * *